United States Patent
Martin et al.

(10) Patent No.: US 9,212,119 B2
(45) Date of Patent: Dec. 15, 2015

(54) METHOD OF MAKING ALPHA, OMEGA-DIIODOPERFLUOROALKANES

(71) Applicant: 3M INNOVATIVE PROPERTIES COMPANY, St. Paul, MN (US)

(72) Inventors: Steven J. Martin, Shoreview, MN (US); Luke T. Dressel, Somerset, WI (US); Aaron E. Hutt, St. Paul, MN (US); Eric A. Schotz, Woodbury, MN (US); Terence D. Spawn, Stillwater, MN (US); Miguel A. Guerra, Woodbury, MN (US); Tatsuo Fukushi, Woodbury, MN (US); Jeremy A. Miller, Eagan, MN (US); Christopher M. Geise, St. Paul, MN (US); James A. McDonell, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/434,981

(22) PCT Filed: Oct. 9, 2013

(86) PCT No.: PCT/US2013/064109
§ 371 (c)(1),
(2) Date: Apr. 10, 2015

(87) PCT Pub. No.: WO2014/062450
PCT Pub. Date: Apr. 24, 2014

(65) Prior Publication Data
US 2015/0259270 A1    Sep. 17, 2015

Related U.S. Application Data

(60) Provisional application No. 61/715,059, filed on Oct. 17, 2012.

(51) Int. Cl.
| | | |
|---|---|---|
| C07C 21/18 | (2006.01) | |
| C07C 45/58 | (2006.01) | |
| C07C 17/26 | (2006.01) | |
| C07C 17/093 | (2006.01) | |

(52) U.S. Cl.
CPC .............. *C07C 45/58* (2013.01); *C07C 17/093* (2013.01); *C07C 17/26* (2013.01)

(58) Field of Classification Search
CPC ............................ C07C 17/093; C07C 17/361
USPC ......................................................... 570/142
See application file for complete search history.

(56) References Cited

U.S. PATENT DOCUMENTS

| | | | |
|---|---|---|---|
| 3,226,449 A | 12/1965 | Blanchard | |
| 3,475,299 A | 10/1969 | Slager | |
| 4,973,633 A | 11/1990 | Moore | |
| 5,032,655 A | 7/1991 | Moore | |
| 5,068,471 A | 11/1991 | Paul | |
| 5,504,248 A | 4/1996 | Krusic | |
| 5,717,036 A | 2/1998 | Saito | |
| 6,002,055 A * | 12/1999 | Yang | B01J 23/74 |
| | | | 570/142 |
| 6,566,471 B1 | 5/2003 | Arcella | |
| 6,646,077 B1 | 11/2003 | Lyons | |

FOREIGN PATENT DOCUMENTS

WO    WO 97-30957    8/1997

OTHER PUBLICATIONS

Yang, Zhen Yu. Environmentally Benign Processes for Making Useful Fluorocarbons: Nickel- or Copper (I) Iodide-Catalyzed Reaction of Highly Fluorinated Epoxides with Halogens in the Absence of Solvent and Thermal Addition of CF212 to Olefins. Journal of Organic Chemistry, 2004, vol. 69, 2394-2403.*

Yang, Zhen Yu. Nickel-Catalyzed Reaction of Highly Fluorinated Epoxides with Halogens. Journal of the American Chemical Society, 1996, vol. 118, 81401-8141.*

"Alloy Information Report for Hastelloy C", 2008, [retrieved from the internet on Aug. 7, 2012], URL<http://www.steelforge.com/forgings/alloys/hastelloycreport.php>, 2pgs.

"Fluorine-Containing Polymers, Perfluoroepoxides", Kirk-Othmer Encyclopedia of Chemical Technology, 2000, 11pgs.

(Continued)

*Primary Examiner* — Sikarl Witherspoon
(74) *Attorney, Agent, or Firm* — Bradford B. Wright

(57) ABSTRACT

A method of making α,ω-diiodoperfluoroalkanes includes combining: diatomic iodine, at least one perfluoroalkylene oxide represented by the formula wherein $R_f$ represents a perfluoroalkyl group; and at least one of: a) a first metallic compound comprising nickel, and a second metallic compound comprising molybdenum that is compositionally different from the first metallic compound; or b) a metallic alloy comprising from 50 to 70 percent by weight of nickel and from 20 to 40 percent by weight of molybdenum, based on the total weight of the metallic alloy, thereby producing at least one product represented by the formula $I(CF_2)_nI$, wherein n independently represents an integer in the range of from 1 to 11. The total weight of the at least one product wherein n is 3 or greater exceeds the total weight of the at least one product wherein n is 1 or 2 by a factor of at least 4.

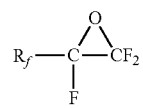

(I)

22 Claims, No Drawings

(56) References Cited

OTHER PUBLICATIONS

"Hastelloy", Wikipedia, [retrieved from the Internet on Jul. 15, 2012], URL<http://en.wikipedia.org/wiki/Hastelloy>, pp. 2.
Haynes Intl, "Products and Capabilities", 2011, 6 pgs.
Haynes Intl, "Hastelloy B-2 Alloy", 1997, 12 pgs.
Yang, "Environmentally Benign Processes for Making Useful Fluorocarbons: Nickel- or Copper(I) Iodide-Catalyzed Reaction of Highly Fluorinated Epoxides with Halogens in the Absence of Solvent and Thermal Addition of CF2I2 to Olefins", Journal of Organic Chemistry, 2004, vol. 69, pp. 2394-2403.
International Search Report for PCT International Application No. PCT/US2013/064109, mailed on May 9, 2014, 3pgs.

* cited by examiner

METHOD OF MAKING ALPHA, OMEGA-DIIODOPERFLUOROALKANES

TECHNICAL FIELD

The present disclosure broadly relates to methods of making compounds having the formula $I(CF_2)_nI$ wherein n is an integer in the range of 1 to 11.

BACKGROUND

α,ω-Diiodoperfluoroalkanes (e.g., $I(CF_2)_nI$ where n=3-11) are typically expensive and difficult to obtain in large quantity. For example, α,ω-diiodooctafluorobutane can be prepared from tetrafluoroethylene (TFE) and iodine ($I_2$) by the reactions of iodine addition and telomerization. However, the intermediate material 1,2-diiodotetrafluoroethane ($C_2$) is toxic, and tetrafluoroethylene is difficult to handle because of its reactivity. Diiododifluoromethane is likewise hazardous. It would be desirable to have methods of making α,ω-diiodoperfluoroalkanes in high yield and/or with little or no $C_1$ and $C_2$ homologous side products.

SUMMARY

In one aspect, the present disclosure provides a method of making α,ω-diiodoperfluoroalkanes, the method comprising combining components comprising:
i) diatomic iodine;
ii) a perfluoroalkylene oxide represented by the formula

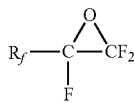

wherein $R_f$ represents a perfluoroalkyl group; and
iii) at least one of:
a) a first metallic compound comprising nickel; and
  a second metallic compound comprising molybdenum that is compositionally different from the first metallic compound; or
b) a metallic alloy comprising from 50 to 70 percent by weight of nickel and from 20 to 40 percent by weight of molybdenum, based on the total weight of the metallic alloy.
thereby producing at least one product represented by the formula

wherein n independently represents an integer in the range of from 1 to 11, and wherein on a weight basis, the total weight of the at least one product wherein n is 3 or greater exceeds the total weight of the at least one product wherein n is 1 or 2 by a factor of at least 4.

In a first embodiment (Embodiment 1), component iii) comprises:
a first metallic compound comprising nickel; and
a second metallic compound comprising molybdenum that is compositionally different from the first metallic compound In a second embodiment (Embodiment 2), component iii) comprises:
a metallic alloy comprising from 50 to 70 percent by weight of nickel and from 20 to 40 percent by weight of molybdenum, based on the total weight of the metallic alloy.

In some embodiments, the perfluoroalkylene oxide comprises hexafluoropropylene oxide. In some embodiments, the second metallic compound further comprises nickel.

Unexpectedly, according to the present disclosure, it is possible to make linear α,ω-diiodoperfluoroalkanes according to the formula $I(CF_2)_nI$ with selectivity for products with n≥3 over those having n=1-2. Additionally, the method can be practiced in a chemical reactor in a single step.

As used herein, the term "metallic alloy" refers to an intimate mixture at least two polyvalent metals (e.g., Ni, Mo, Co, Al, Fe, Cr, Mn, V, Ti, and/or W), which may contain additional elements that are not polyvalent metals (e.g., C, P, S, B, and/or Si).

As used wherein, the term "metallic compound" includes to a single metal in its elemental state or an alloy or two or more metals.

Throughout the specification and claims, numerical ranges are inclusive of their endpoints unless otherwise specified.

Features and advantages of the present disclosure will be further understood upon consideration of the detailed description as well as the appended claims.

DETAILED DESCRIPTION

According to the present disclosure, the conversion of perfluoroalkylene oxides into α,ω-diiodoperfluoroalkanes according to the present disclosure may be accomplished by combining components comprising:
i) diatomic iodine;
ii) a perfluoroalkylene oxide represented by the formula

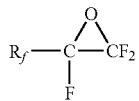

wherein $R_f$ represents a perfluoroalkyl group; and
iii) at least one of:
a) a first metallic compound comprising nickel; and
  a second metallic compound comprising molybdenum that is compositionally different from the first metallic compound; or
b) a metallic alloy comprising from 50 to 70 percent by weight of nickel and from 20 to 40 percent by weight of molybdenum, based on the total weight of the metallic alloy.

Combination of the above components results in formation of one or more products represented by the formula

wherein n independently represents an integer in the range of from 1 to 11.

Advantageously, according to methods of the present disclosure the total combined weight of α,ω-diiodoperfluoroalkanes $I(CF_2)_nI$, wherein n is in the range of from 3 to 11 (i.e., 3, 4, 5, 6, 7, 8, 9, 10, or 11) exceeds the total combined weight of those products having the above formula wherein n is 1 or 2 by a factor of at least 4. Since substantial effort is typically made to reduce and/or eliminate the compounds wherein n is 1 or 2 during synthesis of α,ω-diiodoperfluoroalkanes, the present disclosure provides a simpler and more economical method for the synthesis of the more desirable compounds wherein n is in the range of from 3 to 11.

Methods according to the present disclosure are typically carried out in a vessel (termed a "chemical reactor") that confines the components during reaction. Suitable chemical reactors are well-known to those of ordinary skill in the art. During reaction, agitation is typically provided such that the metallic components (e.g., the first metallic compound, second metallic compound, and/or metallic alloy) contact any nonmetallic components (e.g., iodine and/or perfluoroalkylene oxide represented by the formula

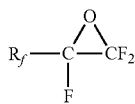

wherein $R_f$ represents a perfluoroalkyl group). In some embodiments, at least one of the metallic components may be present within the liquid phase and/or vapor phase within the chemical reactor. In some embodiments, increased selectivity may be achieved by placing some or all of the metallic components (e.g., those metallic components including molybdenum) at least partially above the liquid phase in the chemical reactor.

A description of the various components that may be used in practice of the present disclosure follows:

The first metallic compound comprises nickel. The nickel may be elemental, or it may be included as an alloy (other than the metallic alloy in component iii) b), hereinabove) comprising at least one other metallic element. Examples of suitable other elements include chromium, iron, tungsten, and cobalt. The first metallic compound may further comprise non-metallic elements such as, for example, silicon, and carbon. To minimize the amount of the first metallic compound needed for rapid reaction, it is generally desirable that the first metallic compound have a relatively high surface area to volume ratio. For example, the first metallic compound may comprise a finely divided powder (e.g., having a particle size of less than about 100 microns). Alternatively, the first metallic compound may be supplied as wire, flakes, filings, balls, or any other form. In one embodiment, the first metallic compound may be supplied as the inner surface for a chemical reactor in which the reaction takes place. In addition to nickel, the first metallic compound may also include molybdenum as long as the second metallic compound comprises molybdenum.

In some embodiments, the first metallic compound comprises at least 16 percent by weight, at least 18 percent by weight, at least 20 percent by weight, at least 22 percent by weight, at least 24 percent by weight, at least 26 percent by weight, at least 28 percent by weight, at least 30 percent by weight, at least 35 percent by weight, at least 40 percent by weight, at least 45 percent by weight, at least 50 percent by weight, at least 55 percent by weight, at least 60 percent by weight, at least 65 percent by weight, at least 70 percent by weight, at least 75 percent by weight, at least 80 percent by weight, at least 85 percent by weight, at least 90 percent by weight, at least 95 percent by weight, at least 99 percent by weight percent, or even at least 100 percent by weight of nickel.

The first metallic compound and the second metallic compound are compositionally different.

To minimize the amount of the first metallic compound needed for rapid reaction, it is generally desirable that the first metallic compound have a relatively high surface area to volume ratio. For example, the first metallic compound may comprise a finely divided powder (e.g., having a mean particle size of less than 100 microns). Alternatively, the first metallic compound may be supplied as wire, flakes, filings, balls, or any other form. In one embodiment, the second metallic compound may be supplied as the inner surface for a chemical reactor in which the reaction takes place.

The second metallic compound comprises molybdenum. The molybdenum may be elemental, or it may be included in an alloy (other than the metallic alloy in component iii) b), hereinabove) comprising at least one other metallic element. Examples of suitable other elements include nickel, chromium, iron, tungsten, and cobalt. The second metallic compound may further comprise non-metallic elements such as, for example, silicon, and carbon. In addition to molybdenum, the second metallic compound may also include nickel as long as the first metallic compound comprises nickel.

In some embodiments, the weight ratio of molybdenum in the second metallic compound to nickel in the first metallic compound is at least 0.28, at least 0.35, or even at least 0.4.

In some embodiments, the second metallic compound comprises at least 16 percent by weight, at least 18 percent by weight, at least 20 percent by weight, at least 22 percent by weight, at least 24 percent by weight, at least 26 percent by weight, at least 28 percent by weight, at least 30 percent by weight, at least 35 percent by weight, at least 40 percent by weight, at least 45 percent by weight, at least 50 percent by weight, at least 55 percent by weight, at least 60 percent by weight, at least 65 percent by weight, at least 70 percent by weight, at least 75 percent by weight, at least 80 percent by weight, at least 85 percent by weight, at least 90 percent by weight, at least 95 percent by weight, at least 99 percent by weight percent, or even at least 100 percent by weight of molybdenum.

In some embodiments, the second metallic element (Embodiment 1) and/or metallic alloy (Embodiment 2) comprises less than 15 percent, less than 12 percent, less than 10 percent, less than 8 percent, less than 6 percent, less than 4 percent, or even less that 2 percent by weight of chromium.

Examples of alloys that may be used in practice of the present disclosure include those alloys having the trade designation "HASTELLOY" (marketed by Haynes International, Kokomo, Ind.) such as those shown in Table 1, below.

TABLE 1

| HASTELLOY GRADE | ELEMENT, percent by weight | | | | | | | |
|---|---|---|---|---|---|---|---|---|
| | Co | Cr | Mo | W | Fe | Si | Mn | C | Ni |
| C-276 | 2.5 | 16 | 16 | 4 | 5 | 0.08 | 1 | 0.01 | 55.41 |
| B-2 | 1 | 1 | 28 | 0 | 2 | 0.1 | 1 | 0.01 | 66.89 |
| B-3 | 3 | 1.5 | 28.5 | 3 | 1.5 | 0.1 | 3 | 0.01 | 59.39 |
| C-4 | 2 | 16 | 16 | 0 | 3 | 0.08 | 1 | 0.01 | 61.91 |
| C-2000 | 2 | 23 | 16 | 0 | 3 | 0.08 | 0 | 0.01 | 55.91 |
| C-22 | 2.5 | 22 | 13 | 3 | 3 | 0.08 | 0.5 | 0.01 | 55.91 |
| G-30 | 2 | 30 | 5.5 | 2.5 | 15 | 1 | 1.5 | 0.03 | 42.47 |
| N | 0.2 | 7 | 16 | 0.5 | 5 | 1 | 0.8 | 0.08 | 69.42 |
| W | 2.5 | 5 | 24 | 0 | 6 | 1 | 1 | 0.12 | 60.38 |
| X | 1.5 | 22 | 9 | 0.6 | 18.5 | 0.5 | 0.5 | 0.1 | 47.3 |

Of these, those metallic alloys marketed under the trade designations HASTELLOY B, HASTELLOY B-2, HASTELLOY B-3, and HASTELLOY W, HYBRID BC1 ALLOY, and HYBRID BC1 ALLOY may be particularly desirable.

Metallic alloys comprising nickel and molybdenum useful in practice of Embodiment 2 comprise from 50 to 70 percent by weight of nickel and from 20 to 40 percent by weight of molybdenum, based on the total weight of the metallic alloy. In some embodiments, the metallic alloy comprises from 55 to 70 percent by weight of nickel, from 50 to 65 percent by weight of nickel, from 55 to 65 percent by weight of nickel, from 55 to 60 percent by weight of nickel, from 60 to 70 percent by weight of nickel, or from 60 to 65 percent by weight of nickel, based on the total weight of the metallic alloy. In some embodiments, the metallic alloy comprises from 20 to 35 percent by weight of molybdenum, from 25 to 40 percent by weight of molybdenum, from 25 to 35 percent by weight of molybdenum, or from 25 to 30 percent by weight of molybdenum, based on the total weight of the metallic alloy.

The above weight ranges of nickel and molybdenum may be combined in any combination to form suitable metallic alloys for practicing the present disclosure. In some embodiments, the weight ratio of molybdenum to nickel in the metallic alloy is at least 0.28.

The perfluoroalkylene oxide is represented by the formula

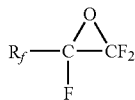

wherein $R_f$ represents a perfluoroalkyl group. In some embodiments, $R_f$ may be linear, branched, and/or cyclic. In some embodiments, $R_f$ comprises from 1 to 12 carbon atoms, more typically from 1 to 6 carbon atoms, more typically from 1 to 4 carbon atoms, and even more typically from 1 to 3 carbon atoms. Examples of useful perfluoroalkylene oxides include hexafluoropropylene oxide, and octafluorobutylene oxide. Suitable perfluoroalkylene oxides are available commercially or can be prepared according to known methods.

The amounts of the components can be adjusted to optimize overall yield and/or relative yield of α,ω-diiodoperfluoroalkanes ($I(CF_2)_nI$) having a specified content of components corresponding to various values of n (e.g., 3, 4, 5, 6, 7, 8, 9, 10, or 11, alone or in any combination). In general, increasing the molar ratio of perfluoroalkylene oxide to diatomic iodine promotes formation of components with higher values of n in the product. For example, by adjusting the amounts of the components (e.g., using a molar ratio of hexafluoropropylene oxide to iodine of at least 3.2, at least 3.6, or even at least 3.9) may be possible to achieve selectivity ($C_{\geq 3}$ to $C_{1-2}$) of at least 4, 5, 6, 7, 8, 9, 10, 15, 20, 30, 50, 75, 100, 150, 200, 250, 300, 400, 500, 1000, 2000, 4000, or even at least 10000. This is highly advantageous, since removal of undesirable $C_1$ and $C_2$ compounds can be laborious and/or costly.

In some embodiments, by adjusting amounts of the components (i.e., perfluoroalkylene oxide, diatomic iodine, and first and second metallic compounds (e.g., Embodiment 1), or metallic alloy (e.g., Embodiment 2)), it is possible to achieve yields of $I(CF_2)_3I$ in excess of 80 percent, in excess of 85 percent, in excess of 90 percent, or even in excess of 95 percent, relative to the total compounds $I(CF_2)_nI$ with n=1-11 combined.

Likewise, in some embodiments, by adjusting amounts of the components (i.e., perfluoroalkylene oxide, diatomic iodine, and first and second metallic compounds (e.g., Embodiment 1), or metallic alloy (e.g., Embodiment 2)), it is possible achieve a total combined weight of the $I(CF_2)_nI$, wherein n=1 or 2 compounds at levels that are less than or equal to 5, 2, or less than or equal to 0.5 weight percent of the total combined weight of the compounds with n=1-11.

In still other embodiments, by adjusting amounts of the components (i.e., perfluoroalkylene oxide, diatomic iodine, and first and second metallic compounds (e.g., Embodiment 1), or metallic alloy (e.g., Embodiment 2)), it is possible achieve a total weight of $CF_2I_2$ at a level that is less than or equal to 5, less than or equal to 3, less than or equal to 2, less than or equal to 0.5, less than or equal to 0.5, less than or equal to 0.1, or even less than or equal to 0.01 weight percent of the total combined weight of the compounds $I(CF_2)_nI$ with n=1-11.

Examples of useful conditions for facilitating one or more of the above embodiments include charging a chemical reactor in which the reaction is carried out using a molar ratio of hexafluoropropylene oxide to diatomic iodine of from 3:1 to 6:1 or from 3:1 to 4:1.

Methods according to the present disclosure may be carried out, for example, in a chemical reactor. Reactor types include tube reactors and stirred reactors. The reactor may be glass-lined and/or metal-lined. If metal-lined, the metal lining may comprise one of the first and second metallic compounds, for example, as discussed hereinabove.

Methods according to the present disclosure can be practiced in batch-wise and/or continuous fashion.

Methods according to the present disclosure can be carried out in any suitable manner as will be apparent to those of ordinary skill in the art. In one embodiment, the first and second metallic compounds are disposed within a chemical reactor (whether as a discrete added component or as part of the reactor lining), then perfluoroalkylene oxide and diatomic iodine are added, for example in amounts as described herein. Typically, the reaction is best carried out under oxygen-free conditions, although this is not a requirement. Reaction progress can be monitored by conventional techniques such as, for example, gas chromatography (optionally in combination with mass spectrometry), thereby allowing one to stop the process when a desired reaction product composition is achieved. Additional variables such as reaction temperature and agitation can be modified, for example, to increase the speed for reaction.

SELECT EMBODIMENTS OF THE PRESENT DISCLOSURE

In a first embodiment, the present disclosure provides a method of making α,ω-diiodoperfluoroalkanes, the method comprising combining components comprising:
  i) diatomic iodine;
  ii) a perfluoroalkylene oxide represented by the formula

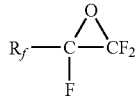

wherein $R_f$ represents a perfluoroalkyl group; and
  iii) at least one of:
    a) a first metallic compound comprising nickel; and
      a second metallic compound comprising molybdenum that is compositionally different from the first metallic compound; or
    b) a metallic alloy comprising from 50 to 70 percent by weight of nickel and from 20 to 40 percent by weight of molybdenum, based on the total weight of the metallic alloy,
thereby producing at least one product represented by the formula

wherein n independently represents an integer in the range of from 1 to 11, and wherein on a weight basis, the total weight of the at least one product wherein n is 3 or greater exceeds the total weight of the at least one product wherein n is 1 or 2 by a factor of at least 4.

In a second embodiment, the present disclosure provides a method according to the first embodiment, wherein component iii) comprises both the first metallic compound and the second metallic compound.

In a third embodiment, the present disclosure provides a method according to the first or second embodiment, wherein the first metallic compound comprises a powder.

In a fourth embodiment, the present disclosure provides a method according to any one of the first to third embodiments, wherein the second metallic compound further comprises nickel, and wherein the weight ratio of the molybdenum to the nickel in the second metallic compound is at least 0.28.

In a fifth embodiment, the present disclosure provides a method according to any one of the first to fourth embodiments, wherein the second metallic compound further comprises nickel, and wherein the weight ratio of the molybdenum to the nickel in the second metallic compound is at least 0.4.

In a sixth embodiment, the present disclosure provides a method according to any one of the first to fifth embodiments, wherein the molybdenum comprises at least 16 percent by weight of the second metallic compound.

In a seventh embodiment, the present disclosure provides a method according to any one of the first to sixth embodiments, wherein the method is carried out in a chemical reactor having an inner surface in contact with the components, and wherein at least a portion of the inner surface comprises the first metallic compound or the second metallic compound.

In an eighth embodiment, the present disclosure provides a method according to the first embodiment, wherein component iii) comprises the metallic alloy.

In a ninth embodiment, the present disclosure provides a method according to the eighth embodiment, wherein the components further comprise a metallic compound comprising nickel.

In a tenth embodiment, the present disclosure provides a method according to the eighth or ninth embodiment, wherein the method is carried out in a chemical reactor having an inner surface in contact with the components, and wherein at least a portion of the inner surface comprises the metallic alloy.

In an eleventh embodiment, the present disclosure provides a method according to any one of the eighth to tenth embodiments, wherein the metallic alloy comprises from 60 to 70 percent of nickel, and 25 to 35 percent of molybdenum, based on the total weight of the metallic alloy.

In a twelfth embodiment, the present disclosure provides a method according to any one of the first to eleventh embodiments, wherein the metallic alloy contains less than 14 percent by weight of chromium.

In a thirteenth embodiment, the present disclosure provides a method according to any one of the first to twelfth embodiments, wherein the factor is at least 50.

In a fourteenth embodiment, the present disclosure provides a method according to any one of the first to thirteenth embodiments, wherein the factor is at least 250.

In a fifteenth embodiment, the present disclosure provides a method according to any one of the first to fourteenth embodiments, wherein the factor is at least 500.

In a sixteenth embodiment, the present disclosure provides a method according to any one of the first to fifteenth embodiments, wherein the at least one perfluoroalkylene oxide comprises hexafluoropropylene oxide.

In a seventeenth embodiment, the present disclosure provides a method according to any one of the first to sixteenth embodiments, wherein the molar ratio of hexafluoropropylene oxide to diatomic iodine is in the range of 3:1 to 6:1.

In an eighteenth embodiment, the present disclosure provides a method according to any one of the first to seventeenth embodiments, wherein the molar ratio of hexafluoropropylene oxide to diatomic iodine is in the range of 3:1 to 4:1.

In a nineteenth embodiment, the present disclosure provides a method of making according to any one of the first to eighteenth embodiments, wherein the total weight of the at least one product wherein n is 1 or 2 comprises less than or equal to 5 weight percent of the total combined weight of the at least one product.

In a twentieth embodiment, the present disclosure provides a method according to any one of the first to the nineteenth embodiments, wherein the total weight of the at least one product wherein n is 1 or 2 comprises less than or equal to 0.5 weight percent of the total combined weight of the at least one product.

In a twenty-first embodiment, the present disclosure provides a method according to any one of the first to the twentieth embodiments, wherein the total weight of $CF_2I_2$ comprises less than or equal to 0.5 weight percent of the total combined weight of the at least one product.

In a twenty-second embodiment, the present disclosure provides a method according to any one of the first to the twenty-first embodiments, wherein the total weight of $CF_2I_2$ comprises less than or equal to 0.01 weight percent of the total combined weight of the at least one product.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. In the Examples and Tables the abbreviation "EX." refers to EXAMPLE, and "COMP. EX." refers to COMPARATIVE EXAMPLE.

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

These abbreviations are used in the following examples: g=gram, hrs=hours, in=inch. Materials and their abbreviations used in the examples are reported in Table 2 (below).

TABLE 2

| MATERIAL | DESCRIPTION |
|---|---|
| Diatomic iodine | obtained from Alpha Aesar, Ward Hill, Massachusetts. |
| HFPO | hexafluoropropylene oxide, available as HFPO from E. I. du Pont de Nemours and Co., Wilmington, Delaware. |
| Nickel | available as NICKEL POWDER, 50-100 MESH, 99.7% |
| Catalyst 1 | METALS BASIS, product # 10579, from Alpha Aesar. |
| Nickel | available as PRO-PAK DISTILLATION PACKING |

TABLE 2-continued

| MATERIAL | DESCRIPTION |
|---|---|
| Catalyst 2 | (0.24") from Cannon Instrument Company, State College, Pennsylvania. This is a nickel ribbon with over 1000 tiny holes per $in^2$ (over 1000 tiny holes per $cm^2$). |
| Nickel Catalyst 3 | Commercially available under the trade name "PRO-PAK DISTILLATION PACKING (0.24")" from Cannon Instrument Company, State College, Pennsylvania. This is a "HASTELLOY C-276" ribbon with over 1000 tiny holes per $in^2$ (over 1000 tiny holes per $cm^2$). |
| Mo wire | Commercially available from Alfa Aesar, Ward Hill, Massachusetts. Annealed wire, 0.5 mm (0.02 in) diameter, 99.5%. The wire as supplied was further etched with 180 grit "WETORDRY TRI-M-ITE" sandpaper from 3M Company, St. Paul, Minnesota. |

Comparative Example A

A 300-mL 316 stainless steel autoclave (available from Superpressure, a subsidiary of Newport Scientific. Jessup, Md.) was charged with 24.5 g of iodine and 2.5 g of Nickel Catalyst 1. The autoclave was then charged with nitrogen and evacuated three times. The autoclave was cooled with dry ice and charged with 58 g of HFPO (3.6 molar ratio of HFPO/iodine). The autoclave was placed in a rocker where it was heated to 170° C. for 12 hrs. The autoclave was allowed to cool to room temperature, and then the gases were vented. A dark liquid (31.3 g) was obtained. The crude mixture was analyzed by $^{19}F$ NMR run in quantitative pulse acquisition mode. Results are reported in Table 3.

Comparative Example B

Comparative Example A was repeated, except Nickel Catalyst 3 was used instead of Nickel Catalyst 1. A dark liquid (36 g) was obtained, which was analyzed by $^{19}F$ NMR run in quantitative pulse acquisition mode. Results are reported in Table 3.

Example 1

Comparative Example A was repeated, except 2.5 g Nickel Catalyst 2 and 2.5 g Nickel Catalyst 3 were used instead of 2.5 g Nickel Catalyst 1. A dark liquid (36 g) was obtained, which was analyzed by $^{19}F$ NMR run in quantitative pulse acquisition mode. Results are reported in Table 3.

Example 2

Comparative Example A was repeated except a 300 mL HASTELLOY B2-lined autoclave (commercially available from Superpressure, subsidiary of Newport Scientific, Jessup, Md.) was used instead of the stainless steel autoclave and 2.5 g Nickel Catalyst 2 was used instead of 2.5 g Nickel Catalyst 1. A dark liquid (36 g) was obtained, which was analyzed by $^{19}F$ NMR run in quantitative pulse acquisition mode. Results are reported in Table 3.

Example 3

Example 3 was run identically to Comparative Example A in the same stainless steel reactor with the same temperature and time but with the addition of 5.0 g Mo (molybdenum) wire (see Table 2) as additional catalyst to Nickel Catalyst 2. Additionally 57 g of HFPO was used instead of 58 g HFPO. The Mo wire as supplied was in a loose coil of about 3 in diameter. This loose coil was forced into the small autoclave so that it was partially submerged in the liquid. This created a gas-liquid interface for the Mo wire.

A dark liquid (33 g) was obtained, which was analyzed by GC chromatography (corrected for response factor). Results are reported in Table 3.

In Table 3, below, percent by weight for Comparative Example A and Example 1 were determined by $^{19}F$ nuclear magnetic resonance ($^{19}F$ NMR) spectroscopy, and Comparative Example B and Examples 2 and 3 were determined using gas chromatography (GC) corrected for response factors.

TABLE 3

| | PERCENT BY WEIGHT | | | | |
|---|---|---|---|---|---|
| IODOCOMPOUNDS | COMP. EX. A | COMP. EX. B | EX. 1 | EX. 2 | EX. 3 |
| $ICF_2I$ | 18 | 24 | 7.4 | 0.0036 | 4.8 |
| $I(CF_2)_2I$ | 0.28 | 0.27 | 0.15 | <0.00005 | 0.12 |
| $I(CF_2)_3I$ | 76 | 72 | 89 | 92 | 85 |
| $I(CF_2)_4I$ | undetected | 0.22 | 0.27 | 0.41 | 0.20 |
| $I(CF_2)_5I$ | 0.086 | 0.20 | 0.47 | 5.4 | 0.01 |
| $I(CF_2)_6I$ | undetected | 0.02 | 0.02 | undetected | 0.03 |
| $I(CF_2)_7I$ | undetected | 0.01 | 0.01 | undetected | 0.05 |
| $I(CF_2)_8I$ | 0.37 | 0.01 | 0.01 | 0.27 | 0.01 |
| $ICF_2CF_2CF(CF_3)C(=O)F$ | 0.11 | NM | NM | 0.23 | NM |
| $CF_3CF(I)CF_2CF_2I$ | 0.17 | NM | NM | 0.16 | NM |
| $CF_3I$ | 0.45 | NM | NM | 0.15 | NM |
| $CF_3CF(I)C(=O)F$ | 0.79 | NM | NM | 0.10 | NM |
| $I(CF_2)_nI$ Weight Ratio (n = 3-11)/(n = 1-2) | 4 | 3 | 12 | $2.7 \times 10^4$ | 18 |

Examples 4-9

Examples 4-9 represent additional reactions run in a larger refurbished (honed out interior surface) 3-liter HASTELLOY B-2-lined reactor with Nickel Catalyst 2. Otherwise, they were run identically to Example 1, except for the variables as reported in Table 4. The autoclave in Examples 4-9 was not insulated while the autoclave for Examples 8 and 9 was insulated, which relates to the batch and jacket temperature information in Table 4. Yields and incorporations are reported in Table 5, and iodocompounds in Table 6.

Example 10

Example 10 was run identically to Example 1 in the same 300 mL HASTELLOY B-2-lined autoclave but without the addition of any additional catalyst. A dark liquid (36 g) was obtained, which was analyzed by GC chromatography (corrected for response factor). Results are reported in Table 6.

TABLE 4

| EXAMPLE | HFPO, grams | IODINE, grams | HFPO:IODINE MOLAR RATIO | NICKEL CATALYST 2, grams | BATCH TEMP., °F. (°C.) | JACKET TEMP., °F. (°C.) | HOLD TIME, hours |
|---|---|---|---|---|---|---|---|
| EX. 4 | 509 | 245 | 3.2 | 50 | 360 (182) | 390-430 (199-221) | 12 |
| EX. 5 | 806 | 343 | 3.6 | 50 | 360 (182) | 390-400 (199-240) | 12 |
| EX. 6 | 865 | 343 | 3.9 | 50 | 365 (185) | 420-425 (216-218) | 12 |
| EX. 7 | 962 | 377 | 3.9 | 55 | 365 (185) | 450 (232) | 13 hrs, 20 min |
| EX. 8 | 1000 | 396 | 3.9 | 60 | 365 (185) | 400 (204) | 12 |
| EX. 9 | 1002 | 396 | 3.9 | 60 | 365 (185) | 378 (192) | 24 |

TABLE 5

| EXAMPLE | YIELD, grams | PERCENT OF IODINE INCORPORATED | PERCENT OF HFPO INCORPORATED |
|---|---|---|---|
| EX. 4 | 343 | 87.0 | 74.6 |
| EX. 5 | 513 | 92.9 | 75.7 |
| EX. 6 | 517 | 91.8 | 72.0 |
| EX. 7 | 566 | 92.0 | 71.8 |
| EX. 8 | 605 | 94.0 | 74.1 |
| EX. 9 | 624 | 94.1 | 78.9 |

TABLE 6

| | PERCENT BY WEIGHT AS DETERMINED BY GAS CHROMATOGRAPHY (corrected for response factor) | | | | | | |
|---|---|---|---|---|---|---|---|
| IODOCOMPOUND | EX. 4 | EX. 5 | EX. 6 | EX. 7 | EX. 8 | EX. 9 | EX. 10 |
| $ICF_2I$ | 10.8 | 3.56 | 0.52 | 0.13 | 0.13 | 0.02 | 0.03 |
| $I(CF_2)_2I$ | 0.17 | 0.06 | 0.02 | 0.01 | 0.01 | undetected | 0.01 |
| $I(CF_2)_3I$ | 83.5 | 92.8 | 94.4 | 94.9 | 95.4 | 84.3 | 94.30 |
| $I(CF_2)_4I$ | 0.30 | 0.41 | 0.46 | 0.52 | 0.51 | 1.43 | 0.36 |
| $I(CF_2)_5I$ | 0.44 | 0.82 | 1.54 | 2.18 | 2.13 | 10.5 | 2.28 |
| $I(CF_2)_6I$ | 0.04 | 0.06 | 0.06 | 0.07 | 0.06 | 0.40 | 0.08 |
| $I(CF_2)_7I$ | 0.06 | 0.08 | 0.07 | 0.07 | 0.06 | 0.86 | 0.05 |
| $I(CF_2)_8I$ | 0.04 | 0.07 | 0.05 | 0.04 | 0.03 | 0.16 | 0.01 |
| $I(CF_2)_9I$ | 0.04 | 0.06 | 0.04 | 0.03 | 0.03 | 0.13 | undetected |
| $ICF_2CF_2CF(CF_3)C(=O)F$ | 0.09 | 0.06 | 0.10 | 0.07 | 0.07 | 0.13 | 0.12 |
| Others | 4.5 | 2.1 | 2.7 | 2.0 | 1.6 | 2.1 | 2.79 |
| $I(CF_2)_nI$ WEIGHT RATIO (n = 3-11):(x = 1-2) | 8 | 26 | 179 | 699 | 702 | $4.89 \times 10^3$ | $2.4 \times 10^3$ |

Other modifications and variations to the present disclosure may be practiced by those of ordinary skill in the art, without departing from the spirit and scope of the present disclosure, which is more particularly set forth in the appended claims. It is understood that aspects of the various embodiments may be interchanged in whole or part or combined with other aspects of the various embodiments. All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:
1. A method of making α,ω-diiodoperfluoroalkanes, the method comprising combining components comprising:
   i) diatomic iodine;
   ii) a perfluoroalkylene oxide represented by the formula

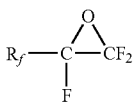

wherein $R_f$ represents a perfluoroalkyl group; and iii) at least one of:
      a) a first metallic compound comprising nickel; and
         a second metallic compound comprising molybdenum that is compositionally different from the first metallic compound; or
      b) a metallic alloy comprising from 50 to 70 percent by weight of nickel and from 20 to 40 percent by weight of molybdenum, based on the total weight of the metallic alloy,
thereby producing at least one product represented by the formula $$I(CF_2)_nI$$

wherein n independently represents an integer in the range of from 1 to 11, and wherein on a weight basis, the total weight of the at least one product wherein n is 3 or greater exceeds the total weight of the at least one product wherein n is 1 or 2 by a factor of at least 4.

2. The method of claim 1, wherein component iii) comprises both the first metallic compound and the second metallic compound.

3. The method of claim 1, wherein the first metallic compound comprises a powder.

4. The method of claim 1, wherein the second metallic compound further comprises nickel, and wherein the weight ratio of the molybdenum to the nickel in the second metallic compound is at least 0.28.

5. The method of claim 1, wherein the second metallic compound further comprises nickel, and wherein the weight ratio of the molybdenum to the nickel in the second metallic compound is at least 0.4.

6. The method of claim 1, wherein the molybdenum comprises at least 16 percent by weight of the second metallic compound.

7. The method of claim 1, wherein the method is carried out in a chemical reactor having an inner surface in contact with the components, and wherein at least a portion of the inner surface comprises the first metallic compound or the second metallic compound.

8. The method of claim 1, wherein component iii) comprises the metallic alloy.

9. The method of claim 8, wherein the components further comprise a metallic compound comprising nickel.

10. The method of claim 1, wherein the method is carried out in a chemical reactor having an inner surface in contact with the components, and wherein at least a portion of the inner surface comprises the metallic alloy.

11. The method of claim 1, wherein the metallic alloy comprises from 60 to 70 percent of nickel, and 25 to 35 percent of molybdenum, based on the total weight of the metallic alloy.

12. The method of claim 1, wherein the metallic alloy contains less than 14 percent by weight of chromium.

13. The method of claim 1, wherein the factor is at least 50.

14. The method of claim 1, wherein the factor is at least 250.

15. The method of claim 1, wherein the factor is at least 500.

16. The method of claim 1, wherein the at least one perfluoroalkylene oxide comprises hexafluoropropylene oxide.

17. The method of claim 16, wherein the molar ratio of hexafluoropropylene oxide to diatomic iodine is in the range of 3:1 to 6:1.

18. The method of claim 16, wherein the molar ratio of hexafluoropropylene oxide to diatomic iodine is in the range of 3:1 to 4:1.

19. The method of claim 1, wherein the total weight of the at least one product wherein n is 1 or 2 comprises less than or equal to 5 weight percent of the total combined weight of the at least one product.

20. The method of claim 1, wherein the total weight of the at least one product wherein n is 1 or 2 comprises less than or equal to 0.5 weight percent of the total combined weight of the at least one product.

21. The method of claim 1, wherein the total weight of $CF_2I_2$ comprises less than or equal to 0.5 weight percent of the total combined weight of the at least one product.

22. The method of claim 1, wherein the total weight of $CF_2I_2$ comprises less than or equal to 0.01 weight percent of the total combined weight of the at least one product.

* * * * *

UNITED STATES PATENT AND TRADEMARK OFFICE
CERTIFICATE OF CORRECTION

PATENT NO. : 9,212,119 B2
APPLICATION NO. : 14/434981
DATED : December 15, 2015
INVENTOR(S) : Martin et al.

Page 1 of 1

It is certified that error appears in the above-identified patent and that said Letters Patent is hereby corrected as shown below:

Column 1
Line 18, Delete "tetratluoroethylene" and insert -- tetrafluoroethylene --, therefor.

Column 1
Line 47, Delete "alloy." and insert -- alloy, --, therefor.

Signed and Sealed this
Second Day of August, 2016

Michelle K. Lee
*Director of the United States Patent and Trademark Office*